United States Patent
Farmer et al.

(10) Patent No.: US 11,964,040 B2
(45) Date of Patent: Apr. 23, 2024

(54) ORAL HEALTH COMPOSITION COMPRISING PURIFIED BIOSURFACTANTS AND/OR THEIR DERIVATIVES

(71) Applicant: Locus Solutions IPCo, LLC, Solon, OH (US)

(72) Inventors: Sean Farmer, North Miami Beach, FL (US); Ken Alibek, Solon, OH (US)

(73) Assignee: Locus Solutions IPCo, LLC, Solon, OH (US)

( * ) Notice: Subject to any disclaimer, the term of this patent is extended or adjusted under 35 U.S.C. 154(b) by 0 days.

(21) Appl. No.: 16/760,635

(22) PCT Filed: Dec. 16, 2018

(86) PCT No.: PCT/US2018/065894
§ 371 (c)(1),
(2) Date: Apr. 30, 2020

(87) PCT Pub. No.: WO2019/133313
PCT Pub. Date: Jul. 4, 2019

(65) Prior Publication Data
US 2020/0345610 A1    Nov. 5, 2020

Related U.S. Application Data

(60) Provisional application No. 62/611,268, filed on Dec. 28, 2017.

(51) Int. Cl.
| | | |
|---|---|---|
| A61K 8/64 | (2006.01) | |
| A61K 8/60 | (2006.01) | |
| A61K 8/69 | (2006.01) | |
| A61Q 11/00 | (2006.01) | |

(52) U.S. Cl.
CPC ............. *A61K 8/64* (2013.01); *A61K 8/60* (2013.01); *A61K 8/69* (2013.01); *A61Q 11/00* (2013.01)

(58) Field of Classification Search
CPC ............. A61Q 11/00; A61Q 1/00; A61Q 1/06
USPC ........................................ 424/49, 404, 234.1
See application file for complete search history.

(56) References Cited

U.S. PATENT DOCUMENTS

| | | | | |
|---|---|---|---|---|
| 4,039,655 | A * | 8/1977 | van der Kerk | A61K 8/69 424/56 |
| 9,585,903 | B2 | 3/2017 | Prabhune et al. | |
| 2002/0123077 | A1 | 9/2002 | O'Toole et al. | |
| 2005/0009747 | A1 | 1/2005 | Kelleher et al. | |
| 2005/0031549 | A1 | 2/2005 | Quay et al. | |
| 2007/0292371 | A1 | 12/2007 | Clarot et al. | |
| 2009/0170932 | A1 | 7/2009 | Aggarwal et al. | |
| 2011/0237531 | A1 | 9/2011 | Yanagisawa et al. | |
| 2012/0039853 | A1 | 2/2012 | Corveleyn et al. | |
| 2013/0331466 | A1 * | 12/2013 | Gross | A61K 31/7028 514/777 |
| 2014/0323747 | A1 | 10/2014 | Kim | |
| 2015/0037302 | A1 | 2/2015 | Bralkowski et al. | |
| 2015/0045290 | A1 | 2/2015 | Coutte et al. | |
| 2015/0150251 | A1 * | 6/2015 | Ernenwein | A61Q 5/00 514/777 |
| 2016/0083757 | A1 | 3/2016 | Fonseca et al. | |
| 2019/0307657 | A1 | 10/2019 | Wenk et al. | |
| 2019/0376021 | A1 | 12/2019 | Alibek et al. | |

FOREIGN PATENT DOCUMENTS

| | | | | |
|---|---|---|---|---|
| CN | 103007287 A | 4/2013 | | |
| EP | 0540074 A1 | 5/1993 | | |
| GB | 2544591 A | 5/2017 | | |
| JP | 2003246717 A | 9/2003 | | |
| JP | 2005298357 | * 10/2005 | ........... | A61K 31/715 |
| JP | 2005298357 A | 10/2005 | | |
| JP | 2005298357 M | * 10/2005 | ........... | A61K 31/715 |
| JP | 2014034552 A | 2/2014 | | |
| WO | 2011134998 A1 | 11/2011 | | |
| WO | 2014120247 A1 | 8/2014 | | |
| WO | 2015153476 A1 | 10/2015 | | |
| WO | 2017044953 A1 | 3/2017 | | |
| WO | 2018049146 A1 | 3/2018 | | |
| WO | 2018049182 A2 | 3/2018 | | |
| WO | 2018094075 A1 | 5/2018 | | |
| WO | 2018129299 A1 | 7/2018 | | |
| WO | 2018148397 A3 | 8/2018 | | |
| WO | 2018148656 A1 | 8/2018 | | |
| WO | 2018191174 A1 | 10/2018 | | |
| WO | 2018195296 A1 | 10/2018 | | |
| WO | 2018208530 A1 | 11/2018 | | |
| WO | 2019022997 A1 | 1/2019 | | |
| WO | 2019023039 A2 | 1/2019 | | |

(Continued)

OTHER PUBLICATIONS

Scapoli et al., "Microflora and periodontal disease." Dental Research Journal, Dec. 2012, vol. 9, issue 8 (Supplemental Issue 2); pp. S202-S206 (Year: 2012).*

(Continued)

*Primary Examiner* — Walter E Webb
(74) *Attorney, Agent, or Firm* — SALIWANCHIK, LLOYD & EISENSCHENK

(57) ABSTRACT

The present invention provides microbe-based products, as well as methods of their production and use, in oral health compositions. More specifically, the present invention provides materials and methods for enhancing and/or maintaining oral health using topical oral health compositions comprising microbial growth by-products, specifically, biosurfactants.

4 Claims, No Drawings

(56) References Cited

FOREIGN PATENT DOCUMENTS

| WO | 2019067380 A2 | 4/2019 |
| --- | --- | --- |
| WO | 2019075456 A3 | 4/2019 |
| WO | 2019089730 A1 | 5/2019 |
| WO | 2019094615 A1 | 5/2019 |
| WO | 2019133315 A1 | 7/2019 |
| WO | 2019133555 A1 | 7/2019 |
| WO | 2019140439 A1 | 7/2019 |
| WO | 2019140440 A1 | 7/2019 |
| WO | 2019227034 A1 | 11/2019 |
| WO | 2020069148 A1 | 4/2020 |
| WO | 2020159842 A1 | 8/2020 |

OTHER PUBLICATIONS

De Brito, D., Biosurfactants from renewable raw materials, Universidade do Minho Departamento de Engenharia Biologica, Nov. 2013, pp. 1-93.

De Oliveira, M., et al., "Review: Sophorolipids a Promising Biosurfactant and it's Applications." International Journal of Advanced Biotechnology and Research, 2015, 6(2): 161-174.

Kurtzman, C.P., et al., "Production of sophorolipid biosurfactants by multiple species of the *Starmerella* (Candida) bombicolayeast clade." FEMS Microbiol Lett, 2010, 311: 140-146.

Morikawa, M., "Beneficial Biofilm Formation by Industrial Bacteria Bacillus subtilis and Related Species." Journal of Bioscience and Bioengineering, 2006, 101(1): 1-8.

Nitschke, M., et al., "Production and properties of a surfactant obtained from Bacillus subtilis grown on cassava wastewater." Bioresource Technology, 2006, 97: 336-341.

Sen, R., "Biosurfactants: Advances in Experimental Medicine and Biology." Landes Bioscience and Springer Science+Business Media, LLC, 2010, 672: 1-331.

Sharma, A. et al., "A study on biosurfactant production in Lactobacillus and *Bacillus* sp." Int. J. Curr. Microbiol. App. Sci., 2014, 3(11): 723-733.

Sil, J., et al., "Health Care Applications of Different Biosurfactants: Review." International Journal of Science and Research (IJSR), 2015, 6(10): 41-50.

Adwan, G., et al., "Synergistic Effects of Plant Extracts and Antibiotics on *Staphylococcus aureus* Strains Isolated from Clinical Specimens." Middle-East Journal of Scientific Research, 2008, 3(3): 134-139.

Coronel-Leon, J., et al., "Optimizing the production of the biosurfactant lichenysin and its application in biofilm control." Journal of Applied Microbiology, 2015, 120: 99-111.

Joshi-Navare, K., et al., "A Biosurfactant-Sophorolipid Acts in Synergy with Antibiotics to Enhance Their Efficiency." Hindawi Publishing Corporation BioMed Research International, 2013, Article ID 512495, pp. 1-8.

Kim, K., et al., "Characteristics of Sophorolipid as an Antimicrobial Agent." J. Microbiol. Biotechnol., 2002, 12(2): 235-241.

Rivardo, F., et al., "Synergistic effect of lipopeptide biosurfactant with antibiotics against *Escherichia coli* CFT073 biofilm." International Journal of Antimicrobial Agents, 2011, 37: 324-331.

Bouassida, M., et al., "Potential application of Bacillus subtilis SPB1 lipopeptides in toothpaste formulation." Journal of Advanced Research, 2017, 8: 425-433.

Elshikh, M., et al., "Rhamnolipids and lactonic sophorolipids: natural antimicrobial surfactants for oral hygiene." Journal of Applied Microbiology, 2017, 123: 1111-1123.

\* cited by examiner

ORAL HEALTH COMPOSITION COMPRISING PURIFIED BIOSURFACTANTS AND/OR THEIR DERIVATIVES

CROSS-REFERENCE TO A RELATED APPLICATION

This application is a National Stage Application of International Application No. PCT/US2018/065894, filed Dec. 16, 2018: which claims priority to U.S. provisional application No. 62/611,268, filed Dec. 28, 2017, which is incorporated herein by reference in its entirety.

BACKGROUND OF THE INVENTION

The oral cavity is comprised of many surfaces, each coated with bacteria that often form bacterial biofilms. Many of these bacteria have been implicated in oral diseases such as caries and periodontitis, which are among the most common bacterial infections in humans. It has been estimated that at least 35% of adults in the United States, aged 30 to 90 years, have periodontitis. In addition, specific oral bacterial species have been implicated in several systemic diseases, such as bacterial endocarditis, aspiration pneumonia, and cardiovascular disease, including atherosclerosis and blood vessel calcification.

Moreover, although the etiology for 70-80% of oral cancers has been mostly linked to tobacco chewing, smoking and alcohol consumption, the remaining percentage of oral cancers have no known risk factors. According to some studies, a significant number of cancers can be attributed to infections involving human papilloma and Epstein Barr viruses, fungi (e.g. *Candida albicans*) and certain oral bacteria. Furthermore, some non-oral cancers are connected to orally developing microorganisms, for example, individuals with *P. gingivalis* have been shown to have an overall 59% increased risk of developing pancreatic cancer.

Many of these conditions result from dental plaque formation, also known as microbial plaque, oral biofilm, dental biofilm, dental plaque biofilm or bacterial plaque biofilm. Thus, it is an important aspect of dental hygiene to remove dental plaque. Furthermore dental plaque can become acidic and cause caries, or can harden into tartar (calculus). Tartar cannot be removed by tooth brushing or with interdental aids, but can only be removed through professional cleaning.

Additionally, many microorganisms of the oral cavity, when allowed to accumulate on tooth and other oral surfaces, can eventually lead to plaque formation, gingivitis, periodontal disease, caries, calculus and halitosis. Early removal of these plaque-forming biofilms can prevent the development of caries and gum diseases, as well as more serious health conditions. Many oral problems start with the formation of biofilms on different oral surfaces, including the teeth and gums. For example, plaques, formed in the presence of food residues and bacteria that are not removed continuously, should be removed by regular oral hygiene treatment.

In addition to routine tooth and mouth cleaning, it is apparent that effective compositions capable of preventing and treating conditions of the oral cavity are essential for oral health. Thus, there is a continuing need for safe, non-toxic compositions that have broad-spectrum cleaning capabilities.

BRIEF SUMMARY OF THE INVENTION

The present invention provides microbe-based products, as well as methods of their production and use, in oral health compositions. More specifically, the present invention provides materials and methods for enhancing and/or maintaining oral health using topical oral health compositions comprising microbial growth by-products. Advantageously, the oral health compositions and methods of the subject invention are environmentally-friendly, non-pharmaceutical, and non-toxic.

In preferred embodiments, the present invention utilizes microorganisms and/or their growth by-products. For example, embodiments of the present invention provide an over-the-counter and/or cosmetic composition for enhancing and/or maintaining oral health, wherein the composition comprises effective amounts of one or more microbial biosurfactants.

The subject compositions are capable of, for example, controlling pathogenic agents in the oral cavity, modulating the oral and nasal mucosal immune response and function, reducing oxidative stress, and enhancing the penetration of anti-biofilm compounds for controlling and removing oral biofilms.

In specific embodiments, the composition comprises one or more purified biosurfactants at a concentration of about 0.01% to about 100% of the final composition. Advantageously, the compositions are non-toxic at concentrations up to at least 5%, and even at concentrations much higher. In certain embodiments, the concentration ranges from about 0.1% to about 5%.

In preferred embodiments, the biosurfactants are purified. Biosurfactants according to the subject invention include, for example, low-molecular-weight glycolipids, cellobiose lipids, lipopeptides, flavolipids, phospholipids, and high-molecular-weight polymers such as lipoproteins, lipopolysaccharide-protein complexes, and/or polysaccharide-protein-fatty acid complexes.

In one embodiment, the biosurfactants comprise glycolipids such as, for example, rhamnolipids (RLP), sophorolipids (SLP), trehalose lipids or mannosylerythritol lipids (MEL). In one embodiment, the biosurfactants comprise lipopeptides, such as, e.g., surfactin, iturin, fengycin, viscosin and/or lichenysin. In one embodiment, the biosurfactants comprise polymeric biosurfactants, such as, for example, emulsan, lipomanan, alasan, and/or liposan.

In some embodiments, a combination of different biosurfactants and/or derivatives of the biosurfactants can be included in the composition.

In certain embodiments, the composition comprises glycolipids, such as, for example, SLP and/or MEL, and/or derivatives thereof.

In some embodiments, the SLP is in a lactonic or acidic form. In some embodiments, use of acidic form SLP enhances the foaming and cleansing capabilities of the composition when used as, for example, a toothpaste.

In certain embodiments, the composition can also comprise lipopeptides, such as, for example, surfactin and/or derivatives thereof.

One embodiment comprises one or more glycolipids with one or more lipopeptides, for example, MEL, SLP and/or MEL or SLP derivatives with surfactin and/or surfactin derivatives.

In certain embodiments, the biosurfactants used according to the present invention are capable of enhancing penetration of active components of an oral pharmaceutical product, for example, a topical analgesic used for dental procedures, without being characterized as a pharmaceutical product; thus the biosurfactants serve as adjuvants, to enhance the effectiveness of the treatment. Additionally, the biosurfactants can be useful as active ingredients themselves for enhancing and/or maintaining dental and/or oral health.

The composition can be formulated as, e.g., a suspension, an emulsion, a hydrogel, a paste, a multiphase solution, a vesicular dispersion, a liquid, a gel, or a powder, for use in, e.g., a toothpaste, a mouthwash, a mouth and/or throat spray, a lozenge, a breath mint, a pen or tube with a brush, sponge, or nozzle applicator, a dissolvable strip, an adhesive tape for the teeth, a toothpick, a chewing gum, a tongue scraper, a lip balm, a syringe, a nasal aspirator, a dental floss and/or any other oral care product known in the art.

In some embodiments, the subject invention provides methods of enhancing and/or maintaining the oral health of a mammalian subject, wherein a composition of the subject invention is applied to one or more surfaces of the subject's mouth, lips or oral cavity.

The one or more surfaces can include, for example, the subject's teeth, gums, tongue, palate, floor, roof, throat, pharynx, tonsils, cheeks, lips (interior and exterior), epiglottis, and any of the tissues or passageways connected thereto.

In certain embodiments, the subject is a human or a domesticated animal (e.g., a pet dog or cat). Particularly when the subject is a non-human animal, the method can comprise applying the composition to drinking water and allowing the subject to take the water and composition into the mouth and swallow it. The composition can also be applied to chew toys and bones for an animal to chew on.

In some embodiments, the method further comprises rinsing the composition from the one or more surfaces of the mouth, lips or oral cavity. This can be performed with, for example, water or mouth wash.

In preferred embodiments, the method can be used to treat and/or prevent plaque, biofilm and/or tartar formation; halitosis; oral infections/abscesses; mouth sores, including ulcers, cold sores and/or canker sores; stained teeth; thrush; oral cancers; gingivitis; tooth decay; periodontal disease; caries; and/or any other oral health condition caused by the presence of bacteria, fungi and/or viruses, such as, e.g., inflammatory conditions, tonsillitis, pharyngitis, laryngitis, glossitis, stomatitis and others.

In certain embodiments, the method can be used for reducing the number of undesirable microorganisms present in a subject's oral cavity, thus allowing for an increase in beneficial and/or commensal microflora. For example, the method can be used for controlling microbes that cause plaque and tartar buildup on teeth, halitosis, and those that lead to periodontal disease and/or cavities.

In some embodiments, the method can be used to enhance the healing (e.g., reduce the healing time) of open sores and wounds in the oral cavity, for example, canker sores, cold sores, cuts, bite wounds, burns from hot foods or beverages, surgical incisions and others caused by tissue trauma.

In one embodiment a method is provided for increasing the penetration and/or bioavailability of a dental and/or oral health pharmaceutical compound, wherein a composition of the subject invention is applied with the pharmaceutical compound as an adjuvant. For example, the composition can be administered as an adjuvant for an analgesic, or a gel used for treating canker sores or cold sores. Advantageously, the method can allow for reduced concentrations of the pharmaceutical compound to be administered to the subject in need thereof while remaining therapeutically effective.

In one embodiment, the subject invention provides methods of producing a microbial growth by-product by cultivating a microorganism under conditions appropriate for growth and production of the growth by-product; and, optionally, purifying the growth by-product.

In one embodiment, the microbe-based products of the subject invention are obtained through cultivation processes ranging from small to large scale. The cultivation process can be, for example, submerged cultivation, state fermentation (SSF), and/or modifications, hybrids, or combinations thereof.

DETAILED DESCRIPTION OF THE INVENTION

The present invention provides microbe-based products, as well as methods of their production and use, in oral health compositions. More specifically, the present invention provides materials and methods for enhancing and/or maintaining oral health using topical oral health compositions comprising microbial growth by-products. Advantageously, the oral health compositions and methods of the subject invention are environmentally-friendly, non-pharmaceutical, and non-toxic.

In preferred embodiments, the present invention utilizes microorganisms and/or their growth by-products. For example, embodiments of the present invention provide an over-the-counter and/or cosmetic composition for enhancing and/or maintaining oral health, wherein the composition comprises effective amounts of one or more microbial biosurfactants.

The subject compositions are capable of, for example, controlling pathogenic agents in the oral cavity, modulating the mucosal immune response and function, reducing oxidative stress, and enhancing the penetration of compounds, including those that are useful for killing and removing oral biofilms.

In some embodiments, the subject invention provides methods of enhancing and/or maintaining the dental and/or oral health of a mammalian subject, wherein a composition of the subject invention is applied to one or more surfaces of the subject's mouth, lips or oral cavity. In certain embodiments, the subject is a human or domesticated animal.

Selected Definitions

As used herein the term "enhancing" when used in the context of oral health, means providing a positive change to the mouth, lips and/or oral cavity. The positive change can be permanent or temporary.

Enhancing oral health can also include the treatment of any condition of the mouth, lips and/or oral cavity. The term "treatment" refers to eradicating, reducing, ameliorating, improving, or reversing a degree, sign or symptom of a condition or disorder to any extent, and includes, but does not require, a complete cure of the condition or disorder. Treating can be partially eradicating, reducing, ameliorating, reversing, curing, or improving a disorder.

"Maintaining" oral health means retaining a current state of oral health over an extended period of time. In other words, maintaining oral health means preventing a subject's oral health from experiencing negative change and/or deterioration.

"Preventing" means inhibiting, forestalling or delaying the onset of an event or occurrence. In the context of a disease, condition or disorder, prevention can be, but is not required to be, absolute. This means that the disease, condition or disorder may develop eventually, but at a later time than it would without preventative measures. In some embodiments, prevention means lessening the severity with which a disease, condition or disorder develops.

As used herein, the term "oral health" refers to the health of any part of the internal and external anatomy of the mouth and oral cavity, including the lips. In some embodiments, oral health extends to the health of the pharynx and nasal cavity.

As used herein, the term "oral health condition" encompasses human and animal conditions, disorders, or diseases affecting the mouth, lips and/or oral cavity. Such oral conditions include "dental conditions," which are oral conditions affecting the teeth and gums in particular. Non-limiting examples of oral conditions include infections, biofilms and/or plaques; mouth sores (including ulcers, cold sores and canker sores); stained teeth; as well as conditions that these oral health conditions may cause, e.g., oral cancers, tooth sensitivity, tooth decay and/or loss, cracked teeth, thrush, gum disease, gingivitis, periodontal disease, caries, halitosis, and/or inflammatory conditions, such as, e.g., tonsillitis, pharyngitis, laryngitis, glossitis, and stomatitis.

As used herein, the term "subject" refers to an animal, especially a mammal, needing or desiring enhancement and/or maintenance of dental and/or oral health. The preferred subject in the context of this invention is a human of any gender. The subject can be of any age or stage of development including infant, toddler, adolescent, teenager, adult, and senior. The subject may also be, for example, a dog, cat, horse, or other domesticated mammalian animal.

As used herein, the terms "therapeutically effective amount," "effective amount," and "effective dose" are used to refer to an amount of a compound or composition that, when administered to a subject, is capable of enhancing and/or maintaining oral health in a subject. The actual amount will vary depending on a number of factors including, but not limited to, the particular condition or disorder being treated, the severity of the condition, the size, age, and health status of the subject, and the route of administration.

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of propagule, or a mixture of these. The microbes may be planktonic or in a biofilm form, or a mixture of both. The by-products of growth may be, for example, metabolites (e.g., biosurfactants), cell membrane components, expressed proteins, and/or other cellular components. The microbes may be intact or lysed. The microbes can be present with medium in which they were grown in the microbe-based composition. The cells may be present at, for example, a concentration of $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$ or more CFU/milliliter of the composition. In some embodiments, the microbes are separated from their growth by-products. As used herein, a propagule is any portion of a microorganism from which a new and/or mature organism can develop, including but not limited to, cells, spores, hyphae, conidia, mycelia, buds, cysts, and seeds.

The subject invention further provides "microbe-based products," which are products that are to be applied in practice to achieve a desired result. The microbe-based product can be simply the microbe-based composition harvested from the microbe cultivation process. Alternatively, the microbe-based product may be further processed and/or may comprise further added ingredients. These additional ingredients can include, for example, stabilizers, buffers, appropriate carriers, such as water, salt solutions, or any other appropriate carrier and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, a "biofilm" is a complex aggregate of microorganisms, such as bacteria, wherein the cells adhere to each other. The cells in biofilms are physiologically distinct from planktonic cells of the same organism, which are single cells that can be motile in a liquid medium or on a solid medium.

A "metabolite" refers to any substance produced by metabolism (e.g., a growth by-product) or a substance necessary for taking part in a particular metabolic process. A metabolite can be an organic compound that is a starting material (e.g., glucose), an intermediate (e.g., acetyl-CoA) in, or an end product (e.g., n-butanol) of metabolism. Examples of metabolites include, but are not limited to, enzymes, acids, solvents, gasses, alcohols, proteins, vitamins, minerals, microelements, amino acids, polymers, and surfactants.

As used herein, the term "control" used in reference to a harmful microorganism or a pest means killing, disabling, immobilizing, or reducing population numbers of the harmful microorganism or pest, or otherwise rendering the harmful microorganism or pest substantially incapable of causing harm.

As used herein, an "isolated" or "purified" nucleic acid molecule, polynucleotide, polypeptide, protein or organic compound such as a small molecule (e.g., those described below), is substantially free of other compounds, such as cellular material, with which it is associated in nature. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. A purified or isolated microbial strain means that the strain is removed from the environment in which it exists in nature. Thus, the isolated strain may exist as, for example, a biologically pure culture, or as spores (or other forms of the strain) in association with a carrier.

In certain embodiments, purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

As used herein, "surfactant" means a compound that lowers the surface tension (or interfacial tension) between two liquids or between a liquid and a solid. Surfactants act as e.g., detergents, wetting agents, emulsifiers, foaming agents, and/or dispersants. "Biosurfactants" are surface-active substances produced by a living cell.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, "reduces" means a negative alteration, and "increases" means a positive alteration, wherein the alteration is at least 0.001%, 0.01%, 0.1%, 1%, 5%, 10%, 15%, 20%, 25%, 30%, 35%, 45%, 50%, 55%, 60%, 65%, 70%, 75%, 80%, 85%, 90%, 95%, 99%, or 100%, inclusive of all values therebetween.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless specifically stated or obvious from context, as used herein, the term "or" is understood to be inclusive. Unless specifically stated or obvious from context, as used herein, the terms "a," "and" and "the" are understood to be singular or plural.

Unless specifically stated or obvious from context, as used herein, the term "about" is understood as within a range of normal tolerance in the art, for example, within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

Ranges provided herein are understood to be shorthand for all of the values within the range. For example, a range of 1 to 20 is understood to include any number, combination of numbers, or sub-range from the group consisting 1, 2, 3, 4, 5, 6, 7, 8, 9, 10, 11, 12, 13, 14, 15, 16, 17, 18, 19, 20, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference.

Compositions for Enhancing Oral Health and Formulation Thereof

In preferred embodiments, the present invention utilizes microorganisms and/or their growth by-products. For example, embodiments of the present invention provide an over-the-counter and/or cosmetic composition for enhancing and/or maintaining oral health, wherein the composition comprises effective amounts of one or more microbial biosurfactants.

Advantageously, the oral health compositions and methods of the subject invention are environmentally-friendly, non-pharmaceutical, and non-toxic.

The subject compositions are capable of, for example, controlling pathogenic agents in the oral cavity, modulating the oral and nasal mucosal immune response and function, reducing oxidative stress, and enhancing the penetration of anti-biofilm compounds for controlling and removing oral biofilms.

In specific embodiments, the composition comprises one or more purified biosurfactants at a concentration of about 0.01% to about 100% of the final composition. Advantageously, the compositions are non-toxic at concentrations up to at least 5%, and even at concentrations much higher. In certain embodiments, the concentration ranges from about 0.1% to about 5%.

Biosurfactant molecules consist of hydrophobic and hydrophilic moieties that partition at liquid-liquid and liquid-solid interfaces. These peculiarities can make them effective for a variety of uses related to enhancing and/or maintaining oral health. For example, biosurfactants can be used to remove microscopic coloring particles from teeth without causing damage to the enamel. Additionally, biosurfactants are known to have antifungal, antibacterial, antiviral, and anti-biofilm properties, thus making them effective for, for example, prevention and treatment of plaque and caries, control of excessive microflora in the mouth and oral cavity, as well as reduction of inflammation due to, for example, the different stages of gum disease.

In preferred embodiments, the biosurfactants are purified. Biosurfactants according to the subject invention include, for example, low-molecular-weight glycolipids, cellobiose lipids, lipopeptides, flavolipids, phospholipids, and high-molecular-weight polymers such as lipoproteins, lipopolysaccharide-protein complexes, and/or polysaccharide-protein-fatty acid complexes.

In one embodiment, the biosurfactants comprise glycolipids such as, for example, rhamnolipids (RLP), sophorolipids (SLP), trehalose lipids or mannosylerythritol lipids (MEL). In one embodiment, the biosurfactants comprise lipopeptides, such as, e.g., surfactin, iturin, fengycin, viscosin and/or lichenysin. In one embodiment, the biosurfactants comprise polymeric biosurfactants, such as, for example, emulsan, lipomanan, alasan, and/or liposan.

In some embodiments, a combination of different biosurfactants can be included in the composition. Different isomorphs, variations and derivatives of specific biosurfactants can also be used.

In certain embodiments, the composition comprises glycolipids, such as, for example, SLP and/or MEL, and/or derivatives thereof.

Even more preferably, the composition comprises sophorolipids (SLP) and/or their derivatives. For example, a natural mixture of any of the following forms can be used: unacetylated lactonic, unacetylated acidic, monoacetylated lactonic, monoacetylated acidic, diacetylated lactonic, diacetylated acidic; as well as derivatives, such as: ethyl ester, methyl ester, ethyl ester monoacetate, ethyl ester diacetate, and all others.

In some embodiments, use of acidic form SLP enhances the foaming and cleansing capabilities of the composition when used as, for example, a toothpaste.

Sophorolipids, which are produced by, e.g., *Starmerella bombicola*, are effective cleansing agents that combine with impurities to make the impurities more soluble for easier removal from surfaces. SLPs have antibacterial, antifungal and antiviral activities against a wide spectrum of microbes and pathogens. Furthermore, SLPs provide immunomodulating and anti-inflammatory properties, and act as activators of macrophages and desquamating agents. SLPs have environmental compatibility, high biodegradability, low toxicity, high selectivity and specific activity in a broad range of temperature, pH and salinity conditions.

In some embodiments, the composition can also comprise a lipopeptide, such as, e.g., a surfactin, lichenysin, viscosin, iturin or fengycin.

Surfactin, preferably in the form of sodium surfactin, is produced by *Bacillus* spp. bacteria. It has a high level of surface active functionality, as it is extremely hydrophilic. It forms a transparent gel at a wider range of concentrations than other biosurfactants, and is an effective foaming agent and emulsifier. Additionally, surfactin has antibacterial, antifungal, and antiviral properties, and helps widen the spectrum of antimicrobial activity to reach both Gram-positive and Gram-negative microbes.

In one embodiment, the composition comprises one or more glycolipids with one or more lipopeptides, for example, MEL, SLP, and/or MEL or SLP derivatives, with surfactin and/or surfactin derivatives.

In certain embodiments, the biosurfactants used according to the present invention are capable of enhancing penetration of active components of an oral pharmaceutical product, for example, a topical analgesic used for dental procedures, without being characterized as a pharmaceutical product; thus the biosurfactants can serve as adjuvants, to enhance the effectiveness of a treatment. Additionally, the biosurfactants can be useful as active ingredients themselves for enhancing and/or maintaining dental and/or oral health.

The composition can be formulated as, e.g., a suspension, an emulsion, a hydrogel, a paste, a multiphase solution, a vesicular dispersion, a liquid, a gel, or a powder, for use in, e.g., a toothpaste, a mouthwash, a mouth and/or throat spray, a lozenge, a breath mint, a pen or tube with a brush, sponge, or nozzle applicator, a dissolvable strip, an adhesive tape for the teeth, a toothpick, a chewing gum, a tongue scraper, a lip balm, a syringe, a nasal aspirator, a dental floss and/or any other oral care product known in the art.

In some embodiments, the composition can further comprise additional adjuvants and other additives, such as, e.g., organic solvents, silicones, thickeners, softeners, moisturizers, abrasives, humectants, thickeners, preservatives, fluoride sources, flavoring agents, chelating agents, sweeteners, vitamins, coloring agents, fragrances, carriers or any other ingredients ordinarily formulated into dental and/or oral health compositions.

In certain embodiments, the composition comprises a physiologically acceptable carrier, meaning a carrier suitable for safe administration to a human subject or other mammal including, without limitation, sterile aqueous or non-aqueous solutions, suspensions, and emulsions. The pharmaceutically acceptable carrier may include one or more of the following agents: solvents, emulsifiers, suspending agents, decomposers, binding agents, excipients, stabilizing agents, chelating agents, diluents, gelling agents, preservatives, lubricants, absorption delaying agents, liposomes, and the like. Examples of non-aqueous solvents include, without limitation, propylene glycol, polyethylene glycol, vegetable oils, and organic esters. Aqueous carriers include, without limitation, water, alcohol, saline, and buffered solutions.

Cultivation of Microorganisms and Production of Microbial Growth by-Products

The microorganisms that can be grown according to the subject methods can be, for example, bacteria, yeast and/or fungi. These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In preferred embodiments, the microorganism is a yeast or fungus. Examples of yeast and fungus species suitable for use according to the current invention, include, but are not limited to, *Acaulospora, Aspergillus, Aureobasidium* (e.g., *A. pullulans*), *Blakeslea, Candida* (e.g., *C. albicans, C. apicola*), *Debaryomyces* (e.g., *D. hansenii*), *Entomophthora, Fusarium, Hanseniaspora* (e.g., H *uvarum*), *Hansenula, Issatchenkia, Kluyveromyces, Mortierella, Mucor* (e.g., *M. piriformis*), *Penicillium, Phythium, Phycomyces, Pichia* (e.g., *P. anomala, P. guielliermondii, P. occidentalis, P. kudriavzevii*), *Pseudozyma* (e.g., *P. aphidis*), *Rhizopus, Saccharomyces* (*S. cerevisiae, S. boulardii sequela, S. torula*), *Starmerella* (e.g., *S. bombicola*), *Torulopsis, Thraustochytrium, Trichoderma* (e.g., *T. reesei, T. harzianum, T. virens*), *Ustilago* (e.g., *U. maydis*), *Wickerhamomyces* (e.g., *W. anomalus*), *Williopsis, Zygosaccharomyces* (e.g., *Z. bailii*).

In one embodiment, the microorganism is any yeast known as a "killer yeast." As used herein, "killer yeast" means a strain of yeast characterized by its secretion of toxic proteins or glycoproteins, to which the strain itself is immune. The exotoxins secreted by killer yeasts are capable of killing other strains of yeast, fungi, or bacteria. Killer yeasts can include, but are not limited to, *Wickerhamomyces, Pichia, Hansenula, Saccharomyces, Hanseniaspora, Ustilago Debaryomyces, Candida, Cryptococcus, Kluyveromyces, Torulopsis, Williopsis, Zygosaccharomyces* and others.

In a specific embodiment, the microbial strain is a *Pichia* yeast selected from *Pichia anomala* (*Wickerhamomyces anomalus*), *Pichia guilliermondii*, and *Pichia kudriavzevii*. *Pichia anomala*, in particular, is an effective producer of exo-β-1,3-glucanase, glycolipid biosurfactants that are capable of reducing surface/interfacial tension of water, as well as various other useful solvents, enzymes and metabolites, such as phytase, glycosidases, ethyl acetate, acetic acid, lactic acid, isopropyl alcohol and ethanol.

In one embodiment, the microorganism is *Starmerella bombicola, Pseudozyma aphidis*, or *Saccharomyces cerevisiae*, which are also effective producers of, for example, glycolipid biosurfactants.

In some embodiments, the microorganisms are bacteria, including Gram-positive and Gram-negative bacteria. Bacteria suitable for use according to the present invention include, for example, *Acinetobacter* (e.g., *A. calcoaceticus, A. venetianus*); *Agrobacterium* (e.g., *A. radiobacter*), *Azotobacter* (*A. vinelandii, A. chroococcum*), *Azospirillum* (e.g., *A. brasiliensis*), *Bacillus* (e.g., *B. amyloliquefaciens, B.*

*firmus, B. laterosporus, B. licheniformis, B. megaterium, B. mucilaginosus, B. subtilis, B. coagulans* GBI-30 (BC30)), *Chlorobiaceae* spp., *Dyadobacter fermenters, Frankia* spp., *Frateuria* (e.g., *F. aurantia*), *Klebsiella* spp., *Microbacterium* (e.g., *M. laevaniformans*), *Pantoea* (e.g., *P. agglomerans*), *Pseudomonas* (e.g., *P. aeruginosa, P. chlororaphis, P. chlororaphis* subsp. *aureofaciens* (*Kluyver*), *P. putida*), *Rhizobium* spp., *Rhodospirillum* (e.g., *R. rubrum*), *Sphingomonas* (e.g., *S. paucimobilis*), and/or *Xanthomonas* spp.

In one embodiment, the microorganism is a *Bacillus* sp., such as, *B. subtilis, B. amyloliquefaciens*, or *B. licheniformis*, which are effective producers of lipopeptide biosurfactants.

In one embodiment, the microbe is a strain of *Pseudomonas* (e.g., *P. aeruginosa*). Preferably, the strain is a producer of glycolipid biosurfactants, including, for example, rhamnolipid biosurfactants.

Other microbial strains including strains capable of accumulating significant amounts of, for example, glycolipids, lipopeptides, mannoprotein, beta-glucan and other metabolites that have useful industrial properties (e.g., bio-emulsifying properties, surface/interfacial tension-reducing properties), can be used in accordance with the subject invention.

The subject invention provides methods for cultivation of microorganisms and production of microbial metabolites and/or other by-products of microbial growth. In one embodiment, the subject invention provides materials and methods for the production of biomass (e.g., viable cellular material), extracellular metabolites (e.g. small molecules and excreted proteins), residual nutrients and/or intracellular components (e.g. enzymes and other proteins).

The growth vessel used for growing microorganisms can be any fermenter or cultivation reactor for industrial use. In one embodiment, the vessel may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In one embodiment, a single type of microbe is grown a reactor system. In alternative embodiments, multiple microbes, which can be grown together without deleterious effects on growth or the resulting product, can be grown in a single reactor system. There may be, for example, 2 to 3 or more different microbes grown in a single reactor at the same time. In some embodiments, the more than one microbes grow symbiotically in the reactor.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of microbes in a sample. The technique can also provide an index by which different environments or treatments can be compared.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method can provide oxygenation to the growing culture. One embodiment utilizes slow motion of air to remove low-oxygen containing air and introduce oxygenated air. In the case of submerged fermentation, the oxygenated air may be ambient air supplemented daily through mechanisms including impellers for mechanical agitation of the liquid, and air spargers for supplying bubbles of gas to the liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, isopropyl, propanol, butanol, pentanol, hexanol, isobutanol, and/or glycerol; fats and oils such as soybean oil, rice bran oil, canola oil, olive oil, corn oil, sesame oil, and/or linseed oil; etc. These carbon sources may be used independently or in a combination of two or more.

In one embodiment, the method comprises use of two carbon sources, one of which is a saturated oil selected from canola, vegetable, corn, coconut, olive, or any other oil suitable for use in, for example, cooking. In a specific embodiment, the saturated oil is 15% canola oil or discarded oil that has been used for cooking.

In one embodiment, the microorganisms can be grown on a solid or semi-solid substrate, such as, for example, corn, wheat, soybean, chickpeas, beans, oatmeal, pasta, rice, and/or flours or meals of any of these or other similar substances.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, sodium chloride and/or sodium carbonate. These inorganic salts may be used independently or in a combination of two or more.

In some embodiments, the method for cultivation may further comprise adding additional acids and/or antimicrobials in the liquid medium before and/or during the cultivation process. Antimicrobial agents or antibiotics are used for protecting the culture against contamination. Additionally, antifoaming agents may also be added to prevent the formation and/or accumulation of foam when gas is produced during cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the liquid medium may be necessary.

The method and equipment for cultivation of microorganisms and production of the microbial by-products can be performed in a batch, quasi-continuous, or continuous processes.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control undesirable bacterial growth.

In one embodiment, the subject invention provides methods of producing a microbial metabolite by cultivating a microbe strain of the subject invention under conditions appropriate for growth and production of the metabolite; and, optionally, purifying the metabolite. In a specific embodiment, the metabolite is a biosurfactant. The metabolite may also be, for example, ethanol, lactic acid, beta-glucan, proteins, amino acids, peptides, metabolic intermediates, polyunsaturated fatty acids, and lipids. The metabolite content produced by the method can be, for example, at least 20%, 30%, 40%, 50%, 60%, 70%, 80%, or 90%.

The biomass content of the fermentation medium may be, for example from 5 g/l to 180 g/l or more. In one embodiment, the solids content of the medium is from 10 g/l to 150 g/l.

The microbial growth by-product produced by microorganisms of interest may be retained in the microorganisms or secreted into the growth medium. In another embodiment, the method for producing microbial growth by-product may further comprise steps of concentrating and purifying the microbial growth by-product of interest. In a further embodiment, the medium may contain compounds that stabilize the activity of microbial growth by-product.

In one embodiment, all of the microbial cultivation composition is removed upon the completion of the cultivation (e.g., upon, for example, achieving a desired cell density, or density of a specified metabolite). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a microbe-free medium or contain cells, spores, mycelia, conidia or other microbial propagules. In this manner, a quasi-continuous system is created.

Advantageously, the methods of cultivation do not require complicated equipment or high energy consumption. The microorganisms of interest can be cultivated at small or large scale on site and utilized, even being still-mixed with their media. Similarly, the microbial metabolites can also be produced at large quantities at the site of need.

Preparation of Microbe-Based Products

One microbe-based product of the subject invention is simply the fermentation medium containing the microorganism and/or the microbial metabolites produced by the microorganism and/or any residual nutrients. The product of fermentation may be used directly without extraction or purification. If desired, extraction and purification can be easily achieved using standard extraction and/or purification methods or techniques described in the literature.

The microorganisms in the microbe-based product may be in an active or inactive form, or the compositions may comprise combinations of active and inactive microorganisms. In some embodiments, the growth by-products of the microorganism is extracted from the medium in which it was produced, and, optionally, purified.

The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

The microbes, growth by-products and/or medium resulting from the microbial growth can be removed from the growth vessel and transferred via, for example, piping for immediate use.

In other embodiments, the composition (microbes, medium, growth by-products, or combinations thereof) can be placed in containers of appropriate size, taking into consideration, for example, the intended use, the contemplated method of application, the size of the fermentation tank, and any mode of transportation from microbe growth facility to the location of use. Thus, the containers into which the microbe-based composition is placed may be, for example, from 1 gallon to 1,000 gallons or more. In other embodiments the containers are 2 gallons, 5 gallons, 25 gallons, or larger.

In certain embodiments, use of unpurified microbial growth by-products according to the subject invention can be superior to, for example, purified microbial metabolites alone, due to, for example, the advantageous properties of the yeast cell walls. These properties include high concentrations of mannoprotein as a part of yeast cell wall's outer surface (mannoprotein is a highly effective bioemulsifier) and the presence of biopolymer beta-glucan (an emulsifier) in yeast cell walls. Additionally, the yeast fermentation product further can comprise biosurfactants and other metabolites (e.g., lactic acid, ethyl acetate, ethanol, etc.) in the culture.

Upon harvesting the microbe-based composition from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, solvents, biocides, other microbes and other ingredients specific for an intended use.

Other suitable additives, which may be contained in the formulations according to the invention, include substances that are customarily used for such preparations. Example of such additives include surfactants, emulsifying agents, lubricants, buffering agents, solubility controlling agents, pH adjusting agents, and stabilizers.

In one embodiment, the composition may further comprise buffering agents including organic and amino acids or their salts. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, ammonium hydroxide, potassium carbonate or bicarbonate, hydrochloric acid, nitric acid, sulfuric acid or a mixture.

In one embodiment, additional components such as an aqueous preparation of a salt or polyprotic acid, such as sodium bicarbonate or carbonate, sodium sulfate, sodium phosphate, sodium biphosphate, can be included in the formulation.

Advantageously, in accordance with the subject invention, the microbe-based product may comprise medium in which the microbes were grown. The product may be, for example, at least, by weight, 1%, 5%, 10%, 25%, 50%, 75%, or 100% growth medium. The amount of biomass in the product, by weight, may be, for example, anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

Methods for Enhancing and/or Maintaining Oral Health

In some embodiments, the subject invention provides methods of enhancing and/or maintaining the oral health of a mammalian subject, wherein a composition comprising one or more microbial biosurfactants, and optionally, other additives or adjuvants, is applied to one or more parts of the subject's mouth, lips and/or oral cavity. Preferably, the composition is an over-the-counter, or cosmetic, oral health composition of the subject invention.

In one embodiment, the method comprises applying the composition directly to a surface of a subject's mouth, lips and/or oral cavity. The surface can include, for example, the subject's teeth, gums, tongue, palate, floor, roof, throat, pharynx, tonsils, cheeks, lips (interior and exterior), epiglottis, and any of the tissues or passageways connected thereto.

As used herein, "applying" can refer to any of the following exemplary modes of application: using a toothbrush to scrub and/or polish the teeth and/or gums with the composition; using a brush or sponge, or a pen fitted with a brush or sponge, to paint or spread the composition onto a surface, e.g., the subject's teeth and gums; adhering temporary strips or tapes having the composition thereon to the teeth for a certain number of minutes, e.g., for 20 to 60 minutes; rinsing and/or swishing the composition inside the mouth (e.g., as a mouthwash); spraying or misting the composition into the mouth; dissolving a strip, lozenge or mint on the tongue or in the cheek; placing the composition into a tooth mold or mouth guard and soaking the teeth in the composition; flossing or picking in between the teeth with a floss or toothpick impregnated or coated with the composition; scraping the tongue with a tongue scraper coated with the composition; using the finger or tube to spread the composition inside or on the lips (e.g., as a mouth sore treatment or lip balm); spraying the composition into the nostrils and to the pharynx (e.g., using a nasal aerator); and/or any other mode of applying dental and/or oral treatments to the surfaces of a subject's mouth, lips and/or oral cavity.

In certain embodiments, the subject is a human or a domesticated mammal. A "domesticated" animal is an animal of a species that has been influenced, bred, tamed, and/or controlled over a sustained number of generations by humans, such that a mutualistic relationship exists between the animal and the human. Domesticated animals can be "pets," which include animals that are raised and cared for by a human for protection and/or companionship, such as, for example, dogs, cats, pigs, goats, horses, hamsters, guinea pigs, squirrels, mice, rats, ferrets, chinchillas, and monkeys. Domesticated animals can also be "livestock," which include animals raised in an agricultural or industrial setting to produce commodities such as food, fiber and labor. Types of animals included in the term livestock can include, but are not limited to, alpacas, llamas, beef and dairy cattle, bison, pigs, sheep, goats, horses, mules, asses, camels, In some embodiments, the animal is a wild or exotic mammal that is being housed in a zoo. Wild or exotic mammals can include, for example, big cats, giraffes, bears, primates, pandas, elephants, sloths, meerkats, rhinoceros, hippos, koalas, lemurs, tapirs, seals, sea lions, otters, skunks, wolves, zebras and many others.

Particularly when the subject is a non-human animal, the method can comprise applying the composition to drinking water and allowing the subject to take the water and composition into the mouth and swallow it. The composition can also be applied to, for example, chew toys and bones for an animal to chew on.

In some embodiments, the method further comprises rinsing the composition from the one or more surfaces of the mouth, lips or oral cavity. This can be performed with, for example, water or mouth wash.

In preferred embodiments, the method can be used to treat and/or prevent plaque, biofilm and/or tartar formation; halitosis; oral infections/abscesses; mouth sores, including ulcers, cold sores and/or canker sores; stained teeth; thrush; oral cancers; gum disease; gingivitis; tooth decay; periodontal disease; caries; Strep throat; and/or any other oral health condition caused by the presence of bacteria, fungi and/or viruses, such as, e.g., inflammatory conditions, tonsillitis, pharyngitis, laryngitis, glossitis, stomatitis and others.

In certain embodiments, the method can be used for reducing the number of undesirable microorganisms present in a subject's oral cavity, thus allowing for an increase in beneficial and/or commensal microflora. Certain microbial taxa have been found within the microbial communities of healthy mouths. These include, for example, *Streptococcus, Actinomyces, Veillonella, Fusobacterium, Porphromonas, Prevotella, Treponema, Nisseria, Haemophilis, Eubacteria, Lactobacterium, Capnocytophaga, Eikenella, Leptotrichia, Peptostreptococcus, Staphylococcus*, and *Propionibacterium*. (Avila 2009).

Most of these microorganisms exist in the oral cavity symbiotically or commensally. These beneficial and/or commensal populations may outcompete or reduce the numbers of pathogenic species, thus preventing them from adhering to surfaces within the oral cavity. (Id.).

However, certain microbes can become pathogenic or undesirable when overgrown, or as a result of other factors, including a decline in health or poor oral hygiene. Undesirable microorganisms can include, for example, microbes that cause halitosis, plaque and tartar buildup on teeth, and those that lead to periodontal disease and/or cavities. Specific, non-limiting examples include, *Porphyromonas gingivalis, Tannerella forsythia, Treponema denticola, Actinobacillus actinomycetemcomitans, Actinomyces naeslundii, Streptococcus mutans, Streptococcus sanguis, Streptococcus cristatus, Streptococcus anginosus, Fusobacterium nuclea-*

*tum, Candida albicans, Lactobacillus* spp., *Bifidobacterium* spp., *Atopobium* spp., *Veillonella* spp., and *Campylobacter* spp.

In one embodiment, a beneficial and/or commensal microorganism can be introduced into the oral cavity along with the subject composition to help in controlling undesirable oral microflora.

In some embodiments, the method can be used to enhance the healing (e.g., reduce the healing time) of open sores and wounds in the oral cavity, for example, canker sores, cold sores, cuts, bite wounds, burns from hot foods or beverages, surgical incisions and others caused by tissue trauma. In certain embodiments, in addition to controlling microbial agents that might infect a wound, the composition can influence fibroblasts and epithelial cells to encourage wound healing.

In one embodiment a method is provided for increasing the penetration and/or bioavailability of a dental and/or oral health pharmaceutical compound, wherein a composition of the subject invention is applied with the pharmaceutical compound as an adjuvant. For example, the composition can be administered as an adjuvant for an analgesic, or a gel used for treating canker sores or cold sores. Advantageously, the method can allow for reduced concentrations of the pharmaceutical compound to be administered to the subject in need thereof while remaining therapeutically effective.

The dosage and the frequency of administration of the microbe-based composition according to the subject methods may vary depending on the following factors: the state of a subject's oral health, the route of administration, and the age, physical condition and response of the subject to be treated.

In one embodiment, the composition is applied in a single dose or in several doses. In certain embodiments, application of the oral health composition may be repeated for a time sufficient to achieve a desired enhancement of oral health, including treatment of a disease, condition or disorder, in the area of application. In order to maintain the desired effect, the method can be continued for as long as the effect is desired. This may entail application at least once, twice or three times daily for at least one week, at least two weeks, at least four weeks, or at least eight weeks or more. Once the application of the topical composition is discontinued, the desired enhancement in oral health may also diminish.

The method may be employed as part of an oral health maintenance regime, or prophylactically, to forestall the development of oral health diseases, conditions or disorders.

Once improvement of the subject's condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Subjects may however require intermittent treatment on a long-term basis upon any recurrence of symptoms.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—Production of Lipopeptides

Fermentation of *Bacillus* spp. bacteria can be performed in a nutrient medium containing (g/L), for example:

| Glucose | 18 |
| --- | --- |
| Powder molasses | 2 |
| Sucrose | 1 |
| $KH_2PO_4$ | 0.5 |
| $Na_2HPO_4 \cdot 7H_2O$ | 2.1 |
| KCl | 0.1 |
| $MgSO_4$ | 0.5 |
| $CaCl_2$ | 0.05 |
| Urea | 2.5 |
| $NH_4Cl$ | 1.24 |
| Yeast extract | 2 |
| Corn peptone | 0.5 |
| TekNova trace element (mL) | 1 |
| pH 6.8 | |

Temperature of cultivation is about 40° C., pH stabilization is from 6.8-7.0, and DO stabilization is at 30% (concentration of oxygen in the air is taken as 100%). Duration of cultivation is 24-32 hours. The final concentration of bacterial culture is no less than $1 \times 10^9$ CFU/ml. The concentration of lipopeptides is 5-10 g/L.

Example 2—Fermentation of *Starmerella Bombicola* for Biosurfactant Production in a 2000 L Gallon Reactor A large-scale, fully enclosed reactor with PLC-operated temperature, pH and DO controls, is used. The reactor has a working volume of 1500 L when growing *S. bombicola* for SLP production.

In some embodiments, the nutrients for SLP production are glucose, urea, yeast extract, canola oil, magnesium sulfate, and potassium phosphate.

The reactor is inoculated with 10 liters of liquid culture grown in inoculum reactors. The duration of the cultivation cycle for SLP production is up to 120 hours, at 25° C. and pH 3.5, with sampling performed once a day.

The final concentration of SLP is 70 gallons, with SLP concentration of 300-400 g/L. The SLP can then be purified using known techniques.

Example 3—Toothpaste Formulation

In a specific embodiment, the composition can be formulated as a toothpaste. The toothpaste can be stored in a squeezable tube or container with a closable nozzle or lid on one end.

The toothpaste composition can include a source of fluoride. A wide variety of fluoride containing materials can be used as a source of fluoride in the toothpaste compositions of the present invention. Representative fluoride ion sources include: sodium fluoride, stannous fluoride, potassium fluoride, sodium monofluorophosphate amine fluorides and mixtures thereof. Sodium fluoride is particularly preferred.

The desired level of fluoride in the toothpaste composition is such that the composition contains about 0.1% fluoride by weight of the composition. The amount is the maximum allowed by the FDA in an over-the-counter fluoride toothpaste. Accordingly, sodium fluoride may be incorporated into the toothpaste composition in an amount of about 0.245% by weight of the composition. This will provide about 0.11% fluoride ion by weight of the composition.

Humectants may be incorporated in the toothpaste compositions of the present invention. Humectants are used to retain moisture in the toothpaste, particularly if the toothpaste could be in prolonged contact with the air. Suitable humectants include glycerin, sorbitol, propylene glycol, other edible polyhydric alcohols, or mixtures thereof, which are admixed with a suitable humectant vehicle, such as water. Humectants can be present in the toothpaste composition at a level of from about 15% to about 70%.

Water can also be present in the toothpaste formulation. Water used in the preparation of commercially suitable toothpastes should preferably be deionized and free of organic impurities. Water can generally comprise about 5% to about 40% by weight of the toothpaste compositions herein.

Surfactants can also be included in the toothpaste composition, including, e.g., anionic, cationic, nonionic, and amphoteric, surfactants, especially anionic surfactants having detergent and foaming properties. The surfactants can be present in the toothpaste composition in an amount from about 0.05% to about 5.0%.

Additional ingredients useful in the toothpaste compositions can include flavoring agents; sweetening agents; antibacterial agents; coloring agents; binding agents; and preservatives. Any of these materials can be present in the toothpaste of this invention in an amount up to about 5%.

Suitable binding agents useful in toothpaste compositions of the present invention include alkali metal carboxymethyl celluloses, hydroxyethyl celluloses, hydroxyethyl carboxymethyl celluloses, natural and synthetic gums, polyvinyl pyrrolidone, starch, water soluble hydrophilic colloidal carboxyvinyl polymers, seaweed colloids and mixtures thereof. In a preferred embodiment, the binder comprises a carboxymethyl cellulose material.

Suitable flavoring agents include oils of wintergreen, peppermint, spearmint, sassafras, clove, and cinnamon. Suitable sweetening agents include saccharin, dextrose, levulose, aspartame, D-tryptophan, acetosulpham, dihydrochalcones, steviol glycosidese, and sodium cyclamate.

Preservatives such as methyl paraben, propyl paraben, and sodium benzoate; and antibacterial agents, such as zinc citrate dihydrate, para-chlorophenyl biguanide, 4-chlorobenzylhydryl biguanide, and 5,6-dichloro-2-guanidinobenzimidazole may also be present in the toothpaste composition.

REFERENCES

Avila, M., D. M. Ojcius, O. Yilmaz. (2009). The Oral Microbiota: Living with a Permanent Guest. *DNA Cell Biol*. August; 28(8): 405-11. ("Avila 2009").

We claim:

1. A method for treating a gum disease, gingivitis and/or periodontal disease in a subject's oral cavity, the method comprising applying a composition consisting essentially of a purified sophorolipid component and a mannosylerythritol lipid to microbial biofilm that is present on a surface of the subject's oral cavity in need of said treatment, wherein said sophorolipid component comprises at least 70% by weight of an acidic form sophorolipid, and wherein the application of said composition causes removal of said biofilm, wherein said biofilm comprises *Porphyromonas* gingiva/is.

2. The method of claim 1, wherein the subject is a human or a domesticated animal.

3. The method of claim 1, wherein the acidic form sophorolipid is an unacetylated acidic sophorolipid, monoacetylated acidic sophorolipid, diacetylated acidic sophorolipid or a combination thereof.

4. The method of claim 1, wherein the microbial biofilm further comprises *Tannerella forsythia* and/or *Treponema denticola*.

* * * * *

UNITED STATES PATENT AND TRADEMARK OFFICE
CERTIFICATE OF CORRECTION

PATENT NO. : 11,964,040 B2
APPLICATION NO. : 16/760635
DATED : April 23, 2024
INVENTOR(S) : Sean Farmer and Ken Alibek Page 1 of 1

It is certified that error appears in the above-identified patent and that said Letters Patent is hereby corrected as shown below:

In the Claims

Column 20,
Line 27, Claim 1, "Porphyromonas gingiva/is." should read -- Porphyromonas gingivalis. --.

Signed and Sealed this
Thirtieth Day of July, 2024

Katherine Kelly Vidal
*Director of the United States Patent and Trademark Office*